(12) United States Patent
Sumian et al.

(10) Patent No.: US 6,340,495 B1
(45) Date of Patent: Jan. 22, 2002

(54) DEVICE INCLUDING A CHROMOPHORIC COMPOSITION TO BE APPLIED TO THE SKIN, A METHOD OF FABRICATING SUCH A DEVICE, AND USES THEREFOR

(75) Inventors: Chryslain Sumian; Franck Pitre, both of Antibes; Serge Mordon, Villeneuve d'Ascq, all of (FR)

(73) Assignee: Galderma Research & Development, Valbonne (FR)

( * ) Notice: Subject to any disclaimer, the term of this patent is extended or adjusted under 35 U.S.C. 154(b) by 0 days.

(21) Appl. No.: 09/207,267

(22) Filed: Dec. 9, 1998

(30) Foreign Application Priority Data

Dec. 16, 1997 (FR) ............................. 97 15953

(51) Int. Cl.$^7$ ..................... A61B 5/103; C08F 2/48; C08J 7/04

(52) U.S. Cl. .................... 427/1; 427/508; 427/511; 424/63

(58) Field of Search .................. 424/401, 63; 427/1, 427/508, 511

(56) References Cited

U.S. PATENT DOCUMENTS

| | | | | |
|---|---|---|---|---|
| 4,007,268 A | * | 2/1977 | Voorhees | 424/200 |
| 5,647,866 A | * | 7/1997 | Zaias et al. | 606/9 |
| 5,928,797 A | * | 7/1999 | Vineberg | 424/401 |
| 5,983,900 A | * | 11/1999 | Clement et al. | 128/898 |

FOREIGN PATENT DOCUMENTS

| | | |
|---|---|---|
| WO | WO 95/29702 | 11/1995 |
| WO | WO 97/28784 | 8/1997 |

OTHER PUBLICATIONS

Fink–Puches, Regina, et al. "Primary Clinical Response and Long–Term Follow–Up of Solar Keratoses Treated with Topically Applied 5–Aminoevulinic Acid and Irradiation by Different Wave Bands of Light", *Journal of Photochemistry and Photobiology B: Biology 41* (1997), pp. 145–151.

Brasseur, Nicole, et al. "Adsorption of Hematoporphyrin onto Polyalkylcyanoacrylate Nanoparticles: Carrier Capacity and Drug Release", *International Journal of Pharmaceutics*, 70 (1991), pp. 129–135.

Chemical Abstracts, vol. 123, No. 17, Oct. 23, 1995, abstract No. 221931, XP–002078606. Calzavara–Pinton, Pier G. "Repetitive Photodynamic Therapy with Topical .delta.–aminolevulinic Acid as an Appropriate Approach to the Routine Treatment of Superficial Non–Melanoma Skin Tumors", *J. Photochem. Photobiol.*, B (1995), 29 (1), 53–7.

Vonarx, V. et al. "Potential Efficacy of the Delta 5–Aminolevulinic Acid Bioadhesive Gel Formulation for the Photodynamic Treatment of Lesions of the Gastrointestinal Tract in Mice", *J. Pharm. Pharmacol.* 1997, 49: pp. 652–656.

* cited by examiner

Primary Examiner—Thurman K. Page
Assistant Examiner—Blessing Fubara
(74) Attorney, Agent, or Firm—Oliff & Berridge, PLC

(57) ABSTRACT

The invention relates to device making it possible to apply a chromophoric composition to the skin, said device including a chromophoric composition containing at least one chromophoric agent. The chromophoric composition is in the form of a layer of constant thickness bonded to one face of backing, at least prior to being applied to the skin, the chromophoric agent or agents being distributed uniformly in said composition, and the type of the composition being chosen such that light energy from laser radiation is transformed locally into heat and/or the chemical structure(s) of the chromophoric agent(s) is/are modified locally.

23 Claims, 1 Drawing Sheet

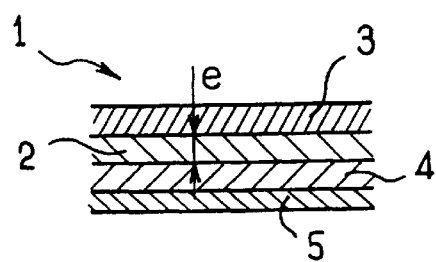
FIG_1
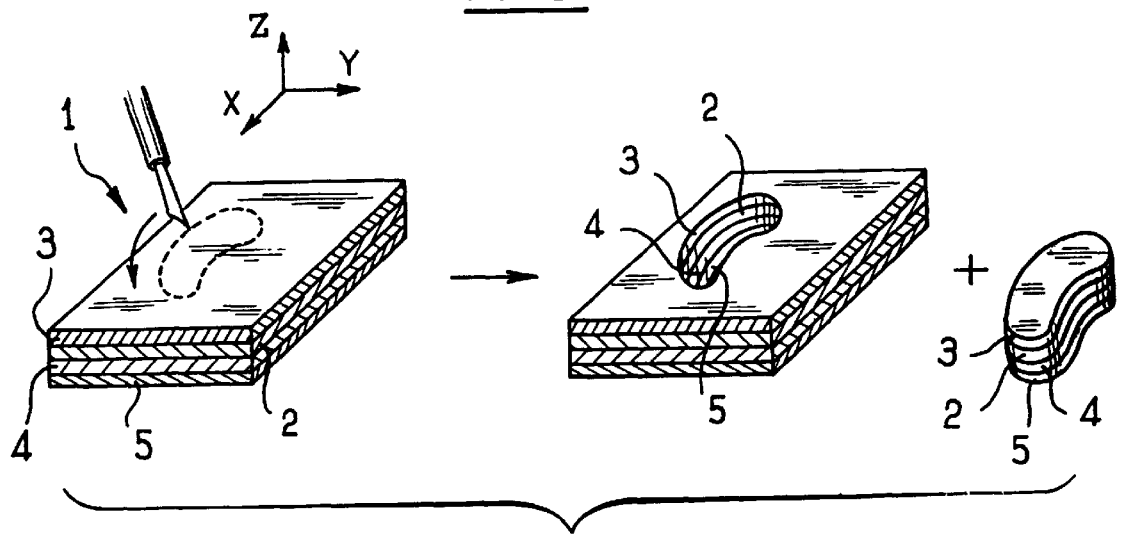
FIG_2
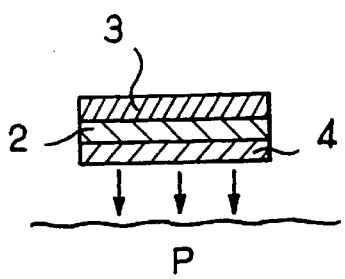
FIG_3
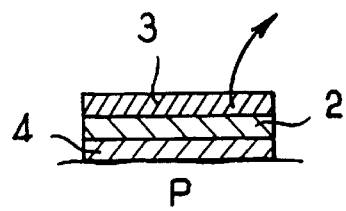
FIG_4
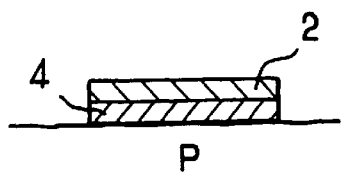
FIG_5
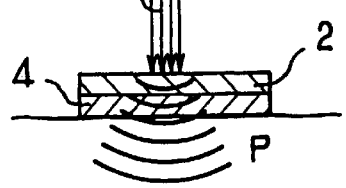
FIG_6

DEVICE INCLUDING A CHROMOPHORIC COMPOSITION TO BE APPLIED TO THE SKIN, A METHOD OF FABRICATING SUCH A DEVICE, AND USES THEREFOR

FIELD OF THE INVENTION

The present invention relates to the general field of treating skin cosmetically or medically by means of laser radiation.

The invention relates particularly to producing heat at the surface of the skin by subjecting a composition comprising at least one chromophoric agent to laser radiation, such a composition being referred to below as a "chromophoric composition".

BACKGROUND OF THE INVENTION

The chromophoric agent(s) absorb(s) light energy from the laser radiation so as to transform said energy into heat and/or so as to modify the chemical structure(s) of the agent(s) under the effect of the laser radiation.

Trials performed by irradiating a chromophoric composition with a laser have shown that it is possible to raise skin temperature locally to more than 100° C. so as to obtain tissue volatilization optionally associated with dermis coagulation.

In the trials, the chromophoric composition was sprayed onto the skin by means of a spray gun, which makes it very difficult to obtain a uniform deposit.

OBJECTS AND SUMMARY OF THE INVENTION

An object of the present invention is to improve the efficacy of cosmetic treatment or medical treatment that uses a chromophoric composition that is subjected to laser radiation.

The present invention achieves this object by providing a device including a chromophoric composition and making it possible to apply the chromophoric composition to the skin, wherein the chromophoric composition is in the form of a layer of constant thickness bonded to one face of backing, at least prior to being applied to the skin, the chromophoric agent or agents being distributed uniformly in said composition, and the type of the composition being chosen such that, under the effect of laser radiation, light energy from the laser radiation is transformed locally into heat and/or the chemical structure(s) of the chromophoric agent (s) is/are modified locally.

The invention makes it easy to deposit a constant thickness of chromophoric composition on the surface of the skin.

The thickness of chromophoric composition on the surface of the skin determines the extent to which the laser radiation is absorbed.

The fact that, in the invention, the thickness of the chromophoric composition is constant and known in advance offers the advantage that the absorbance of the chromophoric composition is defined exactly, and therefore so is the quantity of heat produced on irradiating the composition with the laser radiation.

Thus, the effects of the laser radiation treatment are easier to determine, and the treatment is also easier to reproduce.

An additional advantage of the invention lies in the fact that, since the chromophoric composition is not sprayed, there is no danger of it being dispersed into the atmosphere and being deposited elsewhere than on the region of the skin that is to be treated.

In a particular embodiment, the device includes one or more substances that are in the inactive state in the absence of laser irradiation, and that, under the effect of the laser irradiation, are suitable for transforming into and/or releasing active substances producing effects on the skin.

The invention also provides a method of fabricating a device making it possible to apply a chromophoric composition to the skin, said method including a step consisting in forming a layer of constant thickness of a chromophoric composition, the type of the composition being chosen such that, under the effect of laser radiation, light energy from the laser radiation is transformed locally into heat and/or the chemical structure(s) of the chromophoric agent(s) is/are modified locally.

Preferably, the method includes a step consisting in bonding backing to a layer of determined thickness of a chromophoric composition, at least temporarily.

The invention also provides a method of transforming light energy from laser radiation into heat at the surface of the skin by means of a chromophoric composition, and/or of modifying the chemical structure(s) of one or more chromophoric agents contained in a chromophoric composition at the surface of the skin, said method comprising steps consisting in:

applying a layer of a chromophoric composition to the skin, which layer is of constant thickness and is bonded to backing, at least prior to being applied to the skin, the chromophoric agent(s) being distributed uniformly in said composition;

removing said backing if it is not transparent to the wavelength of the laser used; and irradiating said chromophoric composition by means of a laser, the laser irradiation making it possible to transform light energy from the laser radiation into heat in said layer of chromophoric composition, and or to modify the chemical structure(s) of the chromophoric agent(s), said chromophoric composition having absorbance that, at the emission wavelength of the laser, is such that the light energy transmitted into the skin via said layer of chromophoric composition does not cause any undesired irreversible damage to the tissue or to the cells.

The invention also provides the use of at least one chromophoric agent in fabricating a composition designed to be applied to the surface of the skin, and then to be subjected to laser radiation, the chromophoric composition being in the form of a layer of constant thickness, subjecting said composition to laser irradiation making it possible for light energy from the laser radiation to be transformed locally into heat and/or for the chemical structure(s) of the chromophoric agent(s) to be modified locally.

The invention also provides a method of performing cosmetic treatment, in particular for reducing wrinkles, said method including a step consisting in:

applying a chromophoric composition to the surface of the skin, said composition being in the form of a layer of constant thickness, and the type of the composition being chosen such that, under the effect of laser radiation, the light energy is transformed locally into heat and/or the chemical structure(s) of the chromophoric agent(s) is/are modified locally.

Prior to being applied to the skin, the layer of chromophoric composition may be cut to the format of the region to be treated.

BRIEF DESCRIPTION OF THE DRAWING

Other characteristics and advantages of the present invention appear on reading the following detailed description of a non-limiting implementation of the invention and on examining the accompanying drawing, in which:

FIG. 1 is a cross-section through an embodiment of a device of the invention for applying a chromophoric composition to the skin;

FIG. 2 shows how the device is cut to the desired format; and

FIGS. 3 to 6 show how the composition is applied to the skin and irradiated with laser radiation.

MORE DETAILED DESCRIPTION

FIGS. 1 and 2 show an embodiment of a device 1 of the invention for applying a chromophoric composition to the skin, the device being in the form of a multi-layer structure or film whose total thickness is, for example, greater than 100µm, and preferably less than 3 mm.

The thicknesses of the various layers shown in the figures have been exaggerated to make the drawing clearer.

The device 1 includes a layer 2 of a chromophoric composition, which layer is of predetermined thickness and is bonded via one face to backing 3 and via its opposite face to an adhesive layer 4, itself covered with a protective member 5.

In the Figures, the device 1 extends substantially parallel to a plane defined by the axes X and Y of a rectangular frame of reference XYZ.

In this frame of reference XYZ, the thickness e, measured along axis Z, of the layer 2 of chromophoric composition is constant regardless of position along the axes X and Y.

The chromophoric composition comprises at least one chromophoric agent distributed uniformly at least in all planes parallel to plane XY, and preferably also along the Z axis, distribution being in a solid matrix, preferably a hypoallergenic matrix, and more preferably a matrix that does not diffuse into the skin.

Among the exogenous chromophoric agents that can be used, mention may be made of inorganic compounds such as, for example, carbon black, graphite, and black or red iron oxide, or of organic compounds such as, for example, melanin, indocyanine green, and phthalocyanines and their metallic complexes, and more generally of any inorganic compound or organic compound that absorbs enough light at the wavelength of the laser radiation used.

For the matrix, it is possible, for example, to use an acrylic polymer mixed with a dispersing agent serving to homogenize the distribution of the chromophoric agent(s) in the matrix.

Depending on its/their type(s) and on the type of the matrix, the chromophoric agent(s) may be dispersed as solid particles or as solubilized particles.

Once the device 1 has been fabricated, the chromophoric composition remains in a state which enables it to maintain the thickness given to it.

In addition, the distribution of the chromophoric agent(s) in the matrix remains fixed once the device 1 has been fabricated.

The absorbance of the layer 2 of chromophoric composition and the quantity of heat produced vary as a function of the concentration of the chromophoric agent(s).

The chromophoric agent concentration is chosen such as to obtain the desired effect.

The backing 3 makes it possible to manipulate the device 1 easily prior to applying it to skin.

Preferably, the backing 3 is of constant thickness, and is flexible enough to deform if necessary to match the relief of the skin during application.

In the embodiment described, the backing 3 is constituted by a transparent plastics film making it possible to check, by visual inspection, that the layer 2 of chromophoric composition adheres properly to the skin.

In a variant, the backing 3 may be constituted by a woven fabric or a non-woven fabric, or by a sheet of paper, for example.

The layer of chromophoric composition may be self-adhesive, e.g. by using a self-adhesive matrix, in which case it holds itself against the skin P, or else it may be caused to adhere to the skin by means of an adhesive layer 4, as in the example described.

The adhesive layer 4 is preferably bonded indissociably with the layer 2 of chromophoric composition, and it is constituted by a biocompatible adhesive that is preferably non-hydrophilic, in order to prevent the adhesive power from being modified by the natural hydration of the skin.

In the example described, the adhesive layer 4 is of constant thickness.

The heat resistance characteristics and the heat conduction characteristics of the adhesive are chosen to enable the heat generated within the layer of chromophoric composition during the laser irradiation to be transferred well to the skin.

Preferably, the adhesive layer 4 is self-adhesive, i.e. it does not need an external chemical compound to be used to activate its adhesive-power.

For example, an adhesive of the silicone type or of the synthetic rubber type, such as polyisobutylene may be used to make the adhesive layer 4.

The protective member 5 is constituted by a relatively rigid film that is preferably of constant thickness, and that serves to impart rigidity to the device during packaging, manipulation, and storage, and to facilitate cutting the device to the desired format, if such cutting is necessary.

In the example described, the protective member 5 is more rigid than the backing 3, and it may be constituted by a sheet of card or by a sheet of plastic.

If necessary, the device 1 can be cut in the direction of its thickness by means of a cutting tool, as shown in FIG. 2, to match the contour of the region of the body to be treated.

The layer 2 of chromophoric composition and the backing 3 may be bonded together by interaction of the electrostatic type, or by means of an adhesive layer.

The adhesion between the layer 2 of chromophoric composition and the backing 3 is weaker than the adhesion between the adhesive layer 4 and the skin P, but it is stronger than the adhesion between the adhesive layer 4 and the protective member 5.

If the layer 2 of chromophoric composition is itself adhesive and fixed to the skin without an additional adhesive layer 4, then the adhesion between the backing 3 and the layer 2 of chromophoric composition is weaker than the adhesion between the skin and said layer of chromophoric composition.

The device 1 is used as follows.

If necessary, the multi-layer structure is cut to the desired format by means of a cutting tool, as shown in FIG. 2.

Once the structure has been cut, the protective member 5 is removed, and the adhesive layer 4 is applied against the skin P.

Then, the backing 3 is removed, thereby uncovering the layer 2 of chromophoric composition which is secured to the skin P by means of the adhesive layer 4.

The flexibility of the assembly made up of the layer 2 of chromophoric composition and of the adhesive layer 4 enables it to deform to match cutaneous relief.

By means of a laser, the layer 2 of chromophoric composition is irradiated, thereby causing heat to be given off in said layer, which heat propagates by conduction into the skin P.

It is thus possible to increase the skin temperature locally to more than 100° C., e.g. in order to obtain volatilization optionally associated with coagulation of the dermis.

Preferably, the irradiance of the laser used is less than $10^8$ W/cm$^2$.

The chromophoric agent(s) used is/are preferably chosen to ensure that that fraction of the laser radiation which passes through the layer 2 of chromophoric composition does not cause any undesired irreversible damage to the tissue or cells in the skin P.

Depending on the treatment to be performed, it is possible to vary the thickness of the layer 2 of chromophoric composition so as to obtain the desired release of heat, e.g. to vary the depth of tissue volatilization and/or tissue coagulation.

The device 1 of the invention may be used to remove an unsightly characteristic of the skin, such as wrinkles, warts, atrophic scars and/or hypertrophic scars.

It may also be used, optionally in addition to medication, to treat skin pathologies such as rhinophyma, hyperkeratosis, hyperproliferation of the skin, a psoriasis patch, skin cancer, actinic keratosis, or keloids.

It can also be used to increase the penetration of cosmetically or pharmaceutically active ingredients, or more particularly ingredients that are dermatologically active.

The chromophoric agents used are suitable for the wavelength of the laser radiation used and for obtaining the desired effect.

It is possible to use lasers emitting at wavelengths equal, for example, to 585 nm, 694 nm, 532 nm, 10.6 µm, 2.94 µm, 2.12 µm, or 1.06 µm, with the chromophoric agent(s) being chosen to absorb to a sufficient extent the light energy from the laser radiation at the wavelength in question.

During fabrication of the device, a layer 2 of chromophoric composition that is of constant thickness can be obtained by calendering or extrusion, for example.

The layer 2 of chromophoric composition may be shaped to the desired thickness before it is secured to the backing 3, or, in a variant, the chromophoric composition may be deposited on the backing 3, and then calendered therewith to the desired thickness.

The adhesive layer 4 may be deposited by coating the layer 2 of chromophoric composition.

The device 1 is advantageously made available to practitioners in a sterile package.

Each package corresponds to a given thickness of chromophoric composition, and a range of devices 1 having different thicknesses may be made available to practitioners to enable the practitioners to choose the thickness that is best suited to obtaining the desired result.

Naturally, the invention is not limited to the above-described embodiment.

In particular, when the backing 3 is fully transparent to and inert at the wavelength of the laser radiation used, it is possible to leave the backing in place on the layer 2 of chromophoric composition while it is being irradiated with the laser radiation.

Preferably, the backing 3 is then porous to allow oxygen to pass through it since oxygen can be necessary for the treatment.

In a variant (not shown), the layer of chromophoric composition may be applied directly against the skin, without interposing an adhesive layer that is part of the device.

Also in a variant (not shown), the backing may be microporous and bonded to the layer of chromophoric composition by means of an adhesive layer which is dissolved partially or totally by a solvent with which the backing is imbibed, so as to enable the backing to be removed prior to performing laser irradiation.

The device may further include one or more active substances that act on the skin before or after laser irradiation.

The active substance(s) can take effect on being applied to the skin and/or change state under the effect of the laser radiation and then penetrate into the skin.

The active substance(s) may be contained in the chromophoric composition and/or in the adhesive layer enabling the chromophoric composition to adhere to the skin, when the chromophoric composition is not intrinsically adhesive.

Such an active substance may be an anesthetic or a cicatrizant.

The invention also makes it possible to implement dynamic phototherapy consisting in using a pharmaceutical product in association with a laser, e.g. hematoporphyrin derivative (HPD) which is present in the inactive state in the device and which is transformed under the effect of the laser radiation into an active substance having curative and/or cosmetic properties.

The laser radiation may also cause heat to be given off in the chromophoric composition to make it easier for the active substances contained in the device to penetrate into the skin.

What is claimed is:

1. A device making it possible to apply a chromophoric composition to skin, said device comprising a chromophoric composition containing at least one chromophoric agent, wherein the chromophoric composition is in the form of a layer having a constant thickness and is bonded to one face of a backing, at least prior to being applied to the skin, the at least one chromophoric agent being distributed uniformly in said composition, and the composition being chosen such that after application to the skin light energy from laser irradiation of the composition at least one of a) is transformed locally into heat and b) locally modifies the chemical structure of the at least one chromophoric agent in the composition.

2. A device according to claim 1, wherein said layer of chromophoric composition is bonded removably to said backing.

3. A device according to claim 1, wherein said chromophoric composition is self-adhesive.

4. A device according to claim 1, wherein said layer of chromophoric composition is bonded, by way of its face facing away from the backing, to an adhesive layer.

5. A device according to claim 4, wherein said adhesive layer and the layer of chromophoric composition are bonded together indissociably.

6. A device according to claim 4, wherein adhesion characteristics of said adhesive layer are chosen such that said adhesive layer adheres more strongly to the skin than the backing adheres to the layer of the chromophoric composition.

7. A device according to claim 4, further comprising a removable protective member covering said adhesive layer, and wherein adhesion characteristics of said adhesive layer are chosen such that said adhesive layer adheres more strongly to the layer of the chromophoric composition than to said protective member.

8. A device according to claim 7, wherein said protective member is more rigid than the backing.

9. A device according to claim 1, wherein said backing is transparent to the wavelength of the laser used.

10. A device according to claim 1, wherein said backing is sufficiently flexible to deform so as to match cutaneous relief.

11. A device according to claim 1, further comprising one or more substances suitable for diffusing into the skin under the action of heat that is given off while the chromophoric composition is being irradiated by the laser.

12. A device according to claim 1, further comprising one or more pharmaceutical substances that are active independently of the action of the laser.

13. A device according to claim 1, further comprising one or more substances that are in the an inactive state in the absence of laser irradiation, and that, under the effect of laser irradiation, are suitable for transforming into and/or releasing active substances producing effects on the skin.

14. A method of fabricating a device making it possible to apply a chromophoric composition to skin, said chromophoric composition comprising at least one chromophoric agent, said method including a step of forming a layer of constant thickness of a chromophoric composition, the at least one chromophoric agent being distributed uniformly in said composition, and the composition being chosen such that light energy from laser irradiation of the composition at least one of: a) is transformed locally into heat and b) locally modifies the chemical structure of the at least one chromophoric agent in the composition.

15. A method according to claim 14, further comprising a step of at least temporarily bonding a backing to a layer of determined thickness of the chromophoric composition.

16. A method of transforming light energy from laser radiation into heat at the surface of skin by means of a chromophoric composition comprising at least one chromophoric agent, and/or modifying the chemical structure by laser radiation of at least one chromophoric agent contained in a chromophoric composition at the surface of skin, said laser having a wavelength, said method comprising the steps of:

applying a layer of a chromophoric composition comprising at least one chromophoric agent to the skin, which layer is of constant thickness and is bonded to a backing, at least prior to being applied to the skin, the at least one chromophoric agent being distributed uniformly in said composition, said backing being chosen from the group consisting of backings that are transparent at said wavelength and backings that are not transparent at said wavelength;

removing said backing if it is not transparent at said wavelength; and irradiating said chromophoric composition by means of a laser, the laser irradiation at least one of a) transforming light energy into heat in said layer of chromophoric composition, and b) modifying the chemical structure of the at least one chromophoric agent, said chromophoric composition having absorbance that, at the emission wavelength of the laser, is such that the light energy transmitted to the skin by way of said layer of chromophoric composition does not cause any undesired irreversible damage to skin tissue or to skin cells.

17. A method according to claim 16, wherein said backing is porous, and wherein it is removed by means of a solvent.

18. A method of performing cosmetic treatment, said method comprising the step of:

applying a composition comprising at least one chromophoric agent to the surface of skin, said composition being in the form of a layer of constant thickness, the at least one chromophoric agent being distributed uniformly in said composition, and choosing the composition such that light energy from laser irradiation of the composition at least one of a) transforms locally into heat and b) modifies locally the chemical structure of the at least one chromophoric agent in the composition.

19. A method according to claim 18, wherein, prior to being applied to the skin, the layer of chromophoric composition is cut to a format of a region to be treated.

20. A method according to claim 18, further comprising the step of irradiating said composition with a laser after said composition has been applied to the skin.

21. A device according to claim 12, wherein said substance is an anesthetic.

22. A device according to claim 12, wherein said substance is a cicatrizant.

23. A method according to claim 18, wherein said method is applied for reducing wrinkles.

* * * * *